United States Patent [19]

Martin

[11] Patent Number: 4,860,386
[45] Date of Patent: Aug. 29, 1989

[54] METHOD OF MAKING AN ENCLOSED SLEEVE

[76] Inventor: Mary Ann Martin, 115 E. Embargo St., Rome, N.Y. 13440

[21] Appl. No.: 281,244

[22] Filed: Dec. 7, 1988

Related U.S. Application Data

[62] Division of Ser. No. 86,361, Aug. 17, 1987, Pat. No. 4,815,480.

[51] Int. Cl.4 .......................... A61F 13/00; B32B 7/08; A41D 27/02
[52] U.S. Cl. ...................................... 2/243 R; 2/272; 2/158; 112/441
[58] Field of Search ..................... 112/440, 441; 2/158, 2/159, 160, 161 R, 161 A, 164, 243 R, DIG. 2, 270, 272; 128/879

[56] References Cited

U.S. PATENT DOCUMENTS

| | | |
|---|---|---|
| 1,183,225 | 5/1916 | Overmeyer . |
| 1,296,966 | 3/1919 | Kaufman . |
| 1,537,811 | 5/1925 | Epling . |
| 1,926,194 | 9/1933 | Clark . |
| 1,944,451 | 1/1934 | Newman . |
| 2,030,091 | 2/1936 | Behringer . |
| 2,262,463 | 11/1941 | Marr . |
| 2,465,622 | 3/1949 | Widetsky . |
| 2,505,409 | 4/1950 | Kirchner . |
| 2,675,554 | 4/1954 | Gertz . |
| 2,828,738 | 4/1958 | Strelakos . |
| 2,900,642 | 8/1959 | Bauer . |
| 2,948,900 | 8/1960 | Ebenstein ...................... 2/DIG. 2 X |
| 3,044,517 | 7/1962 | Levi .............................. 2/DIG. 2 X |
| 3,114,915 | 12/1963 | Gross . |
| 3,182,657 | 5/1965 | Zurbuchen . |
| 3,187,345 | 6/1965 | Holford ......................... 2/DIG. 2 X |
| 3,317,923 | 5/1967 | Levi ............................ 2/DIG. 2 X |
| 3,327,320 | 6/1967 | Forsyth . |
| 3,361,132 | 1/1968 | Rentsch, Jr. . |
| 3,476,108 | 11/1969 | Matukas . |
| 4,359,784 | 11/1982 | Harrington . |

Primary Examiner—H. Hampton Hunter
Attorney, Agent, or Firm—Wall and Roehrig

[57] ABSTRACT

A garment (20) for controlling excessive hand activity comprises a body clothing means (22) and a pair of sleeve members (24, 26) which each comprise a control end (28, 30). The control ends (28, 30) each comprise a plurality of envelopes (46, 48, 50, 52, 54). The plurality of envelopes are disposed in substantially concentric relation to each other and each contain an opening thereto. Each of the openings are disposed in substantial alignment with the other and are positioned, configured and dimensioned to receive a portion of a person's arm, wrist and hand.

2 Claims, 4 Drawing Sheets

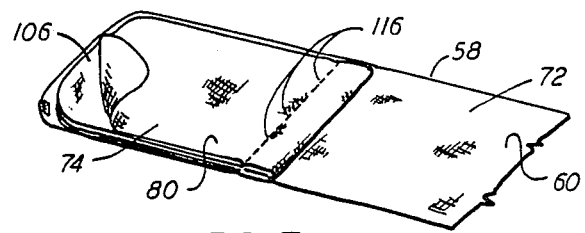
FIG. 7
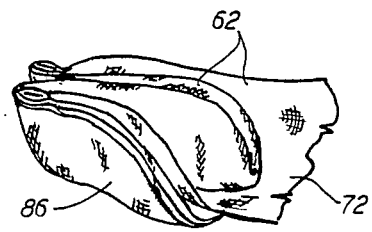
FIG. 10
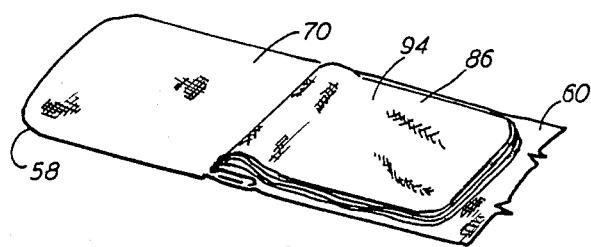
FIG. 8
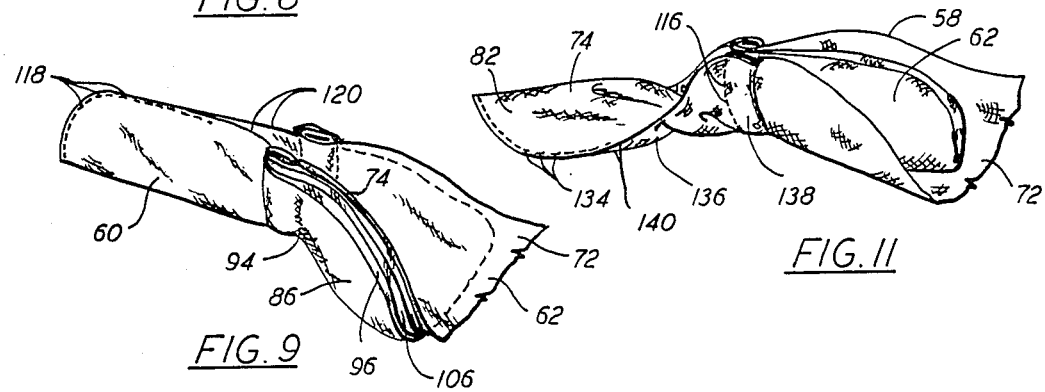
FIG. 9
FIG. 11
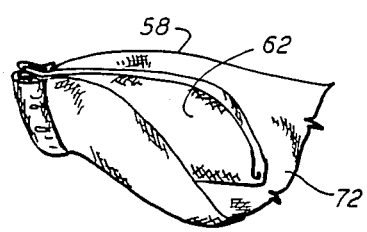
FIG. 12
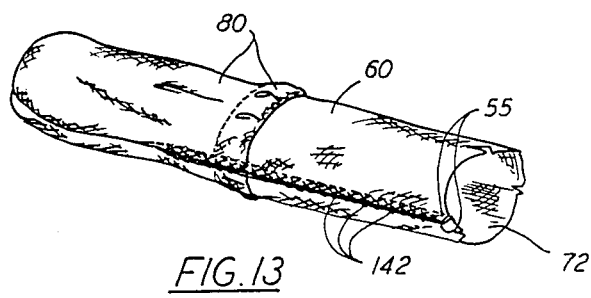
FIG. 13

METHOD OF MAKING AN ENCLOSED SLEEVE

This is a divisional of co-pending application Ser. No. 086,361, filed on Aug. 17, 1987 now U.S. Pat. No. 4,815,480, dated March 28, 1989.

BACKGROUND OF THE INVENTION

The present invention pertains to the field of art involving the treatment and care of people having a compulsion for excessive and destructive hand-activity and a craving for ingesting unnatural articles of food and substances. The present invention relates to a garment which controls and hinders hand activity of the person wearing the garment and provides protection from self-injury.

The abnormal conditions whereby a person experiences a compulsion for excessive and destructive hand activity and a craving for eating unnatural articles of food or substances may be prominent in insane or hysterical people. The hand-activity may include the unraveling and shredding of such person's own clothes; the gathering of foreign articles or substances and putting them to the mouth for ingestion; and inserting the hands into the mouth to be sucked or bitten. The craving for eating unnatural articles or substances may lead to the ingestion of hair, wood, paper, metallic objects or even feces. These abnormal conditions may be manifested in people suffering from a condition called pica. Pica is generally defined as a craving for or eating of unnatural articles of food. It is clear that these conditions may cause serious medical problems with the individual, such as digestive and intestinal complications, and destruction of the tissue of the hand.

In an effort to protect a person suffering from such abnormal conditions one solution has been proposed. This solution involves the use of a garment, such as a shirt, whereby gloves or mittens are sewn to the cuffs of the shirt. When the modified garment is worn, the gloves or mittens act to decrease, somewhat, the dexterity of the hands and cause the person wearing the garment to experience difficulty in picking up foreign objects or substances. In addition, the gloves or mittens act to shield, to a certain extent, the tissue of the hand. However, this solution has been unsuccessful since gloves and mittens do not sufficiently hinder a person from grasping objects and substances that may be brought to the mouth and ingested. In addition, most gloves and mittens may be moistened with water or saliva to aid the person picking up objects such as paper, hair, etc. Moreover, a glove or mitten may ultimately be saturated with water or saliva causing irritation and destruction of hand tissue. Also, a glove or mitten may not sufficiently shield the hand from any biting action of the person. Further, the modified garment may be unraveled and shredded by the person.

In the past, garments and related devices have been employed to restrain certain compulsive activity in individuals. The following patents disclose devices employing some kind of hand enclosure to restrain hand activity: U.S. Patent 3,476,108 to Matuka; U.S. Patent 3,182,657 to Zurbuchen; and U.S. Patent 1,944,451 to Newman. These patented devices utilize stiffening plates or straps disposed about a hand enclosure to restrict hand activity. The devices are unsuitable for precluding an individual from unraveling and shredding the device since the plates are removable, and the straps and stitching are exposed. Further, these devices do not address the compulsive tendency to moisten the exterior surface of the hand enclosure and use it as an aid in picking up substances for ingestion. Moreover, these devices do not protect the hand tissue from long exposure to saliva or water. Further, they are uncomfortable and severly restrictive of hand movement.

SUMMARY OF THE INVENTION

The invention, as claimed, is intended to provide a remedy. It overcomes the problems and satisfies the needs previously indicated. The invention, as claimed, solves the problem of how to control and hinder the compulsive act of picking-up unnatural articles and subtances and ingesting them. In addition, it solves the problem of how to frustrate attempts to collect unnatural objects and substances for ingestion by moistening a hand or glove. Moveover, the invention, as claimed, solves the problem of how to protect the hand tissue from extended exposure to saliva and water. Also, it solves the problem how to shield the hand from self-injury due to compulsive biting of the hand. Further, the invention, as claimed, solves the problem of how to frustrate attempts by the wearer to unravel and shred the protective garment device. The inventive garment, as claimed, overcomes these problems and satisfies these needs in a manner that is comfortable and not severely restrictive to the individual wearer.

In particular, the invention, as claimed, involves the use of a garment such as a shirt or jacket, or jumpsuit, having sleeve members depending therefrom. The sleeve members each comprise a shoulder end and a control end. The sleeve members are connected to said garment at their respective shoulder ends. The control ends are positioned, configured, and dimensioned to enclose a portion of the arm, the wrist and the hand, and comprise a plurality of enclosing envelopes in concentric relation to each other.

BRIEF DESCRIPTION OF DRAWINGS

One way of carrying out the invention is described in detail below with reference to drawings which illustrate only two specific embodiments, in which:

FIGS. 6, 7, 8, 9, 10, 11, 12, and 13 are fragmentary perspective views of a portion of the sleeve and control end of the present invention showing, in progressive steps, the construction thereof, according to the present invention;

DESCRIPTION OF THE PREFERRED EMBODIMENTS

Figure 1:
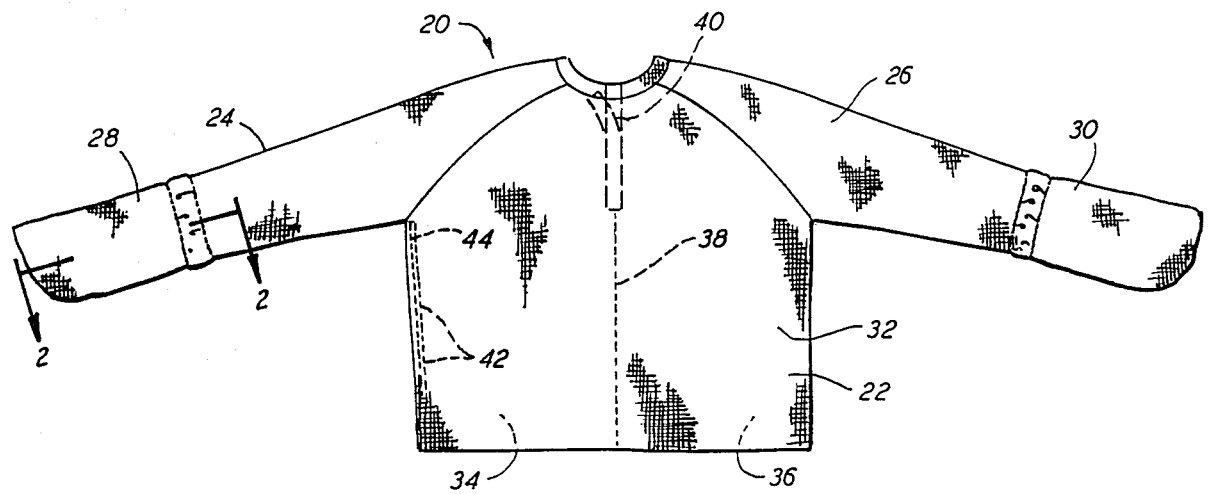
FIG. 1 is a front elevation view of a garment which incorporates the present invention.
Figure 14:
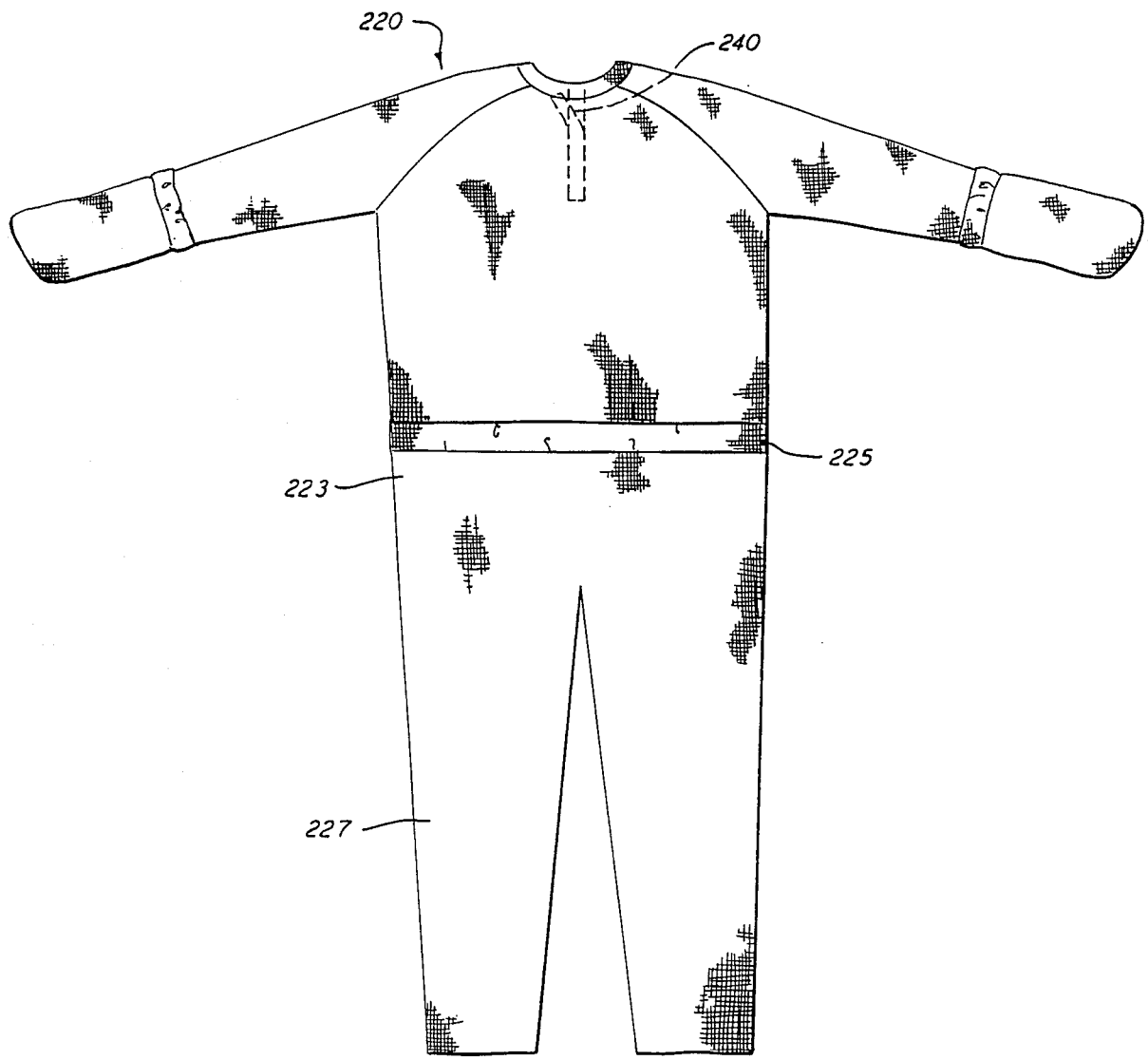
FIG. 14 is a front elevation view of an alternative embodiment of a garment which incorporates the present invention.

Referring to FIG. 1, a garment for restraining hand-activity can be constructed in acordance with the present invention as illustrated. The inventive garment designated generally 20 is provided with a body clothing portion 22, which may be configured as a shirt or jacket body as shown in FIG. 1, or may be configured as a jumpsuit body, having torso and leg portions as shown in FIG. 14. Garment 20 further comprises sleeves designated generally 24 and 26 each having a shoulder end. Sleeves 24 and 26 are connected to body clothing portion 22 at their shoulder ends. Depending from sleeve 24 is a control end 28; and depending from sleeve 26 is a control end 30. Sleeves 24 and 26 may be configured as raglan type sleeves as illustrated in FIG. 1. Body clothing portion 22 comprises a front panal 32 and a pair of rear panels 34 and 36 respectively. Rear panels 34 and 36 are seamed together along a portion of their adjoining edges at a seam 38. The remaining portion of the adjoining edges of rear panels 34 and 36 remain free to form a placket 40 at the rear of body clothing portion 22. It has been empirically determined that a suitable length for placket 40 is approximately ten inches, although other lengths may be used. Placket 40 may be equipped with a means for fastening its edges together, such as Velcro brand fastening material.

Front panel 32 and rear panels 34 and 36 are fastened together by stitched seams. In addition, sleeves 24 and 26 are fastened to body clothing portion 22 by stitched seams. Each of these seams, including seam 38, have seam edges projecting into the interior volume defined by garment 20. The seam edges of each of the seams are sewn together by an overlock stitching 42, and further reinforced together by a straight stitch 44, as illustrated in FIG. 1.

Sleeves 24 and 26 are substantially alike, and therefore a detailed description of one will be sufficient for describing both sleeves 24 and 26. Control ends 28 and 30 are substantially alike, and therefore a detailed description of one will be sufficient for describing both control ends 28 and 30.

Figure 2:
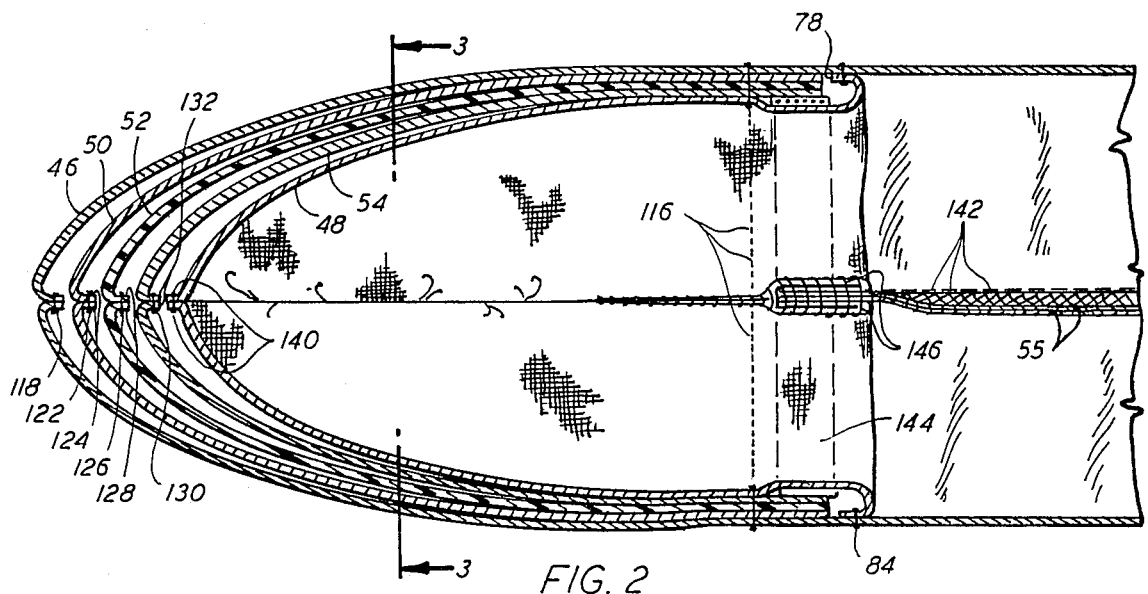
FIG. 2 is a longitudinal sectional view through the control end of the present invention taken on the line 2—2, FIG. 1.
Figure 3:
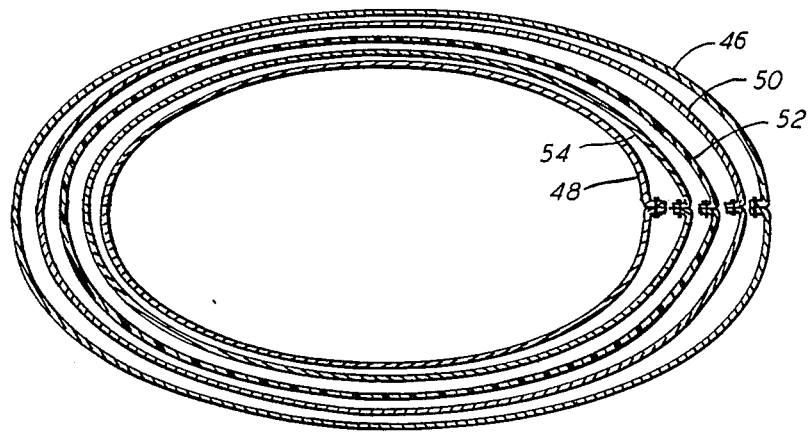
FIG. 3 is a transverse sectional view through a portion of the control end of the present invention taken on the line 3—3, FIG. 2.
Figure 5:
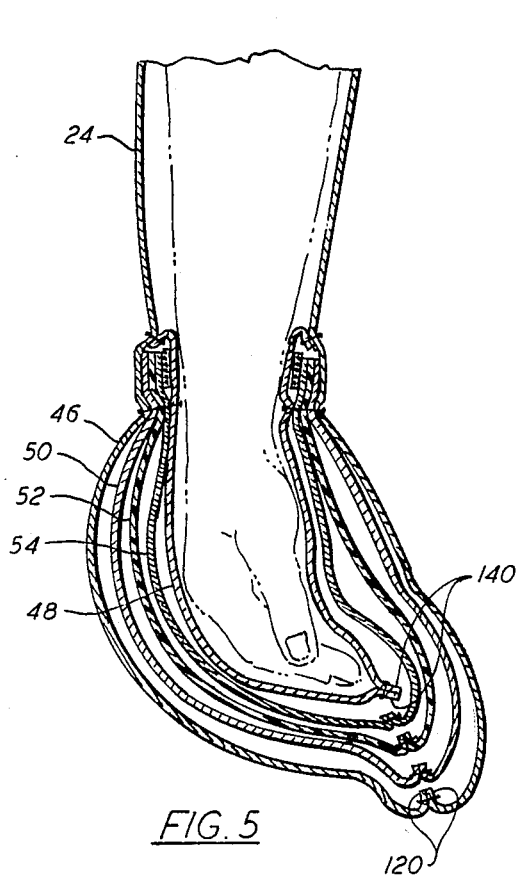
FIG. 5 is a longitudinal sectional view showing the operation of the present invention when the hand of the wearer is moderately flexed inside the control end.

A longitudinal cross-sectional view of control end 28 is illustrated in FIG. 2. Control end 28 comprises a plurality of envelopes disposed in concentric relation to each other, each envelope having an opening thereto which coincides with the openings of the other envelopes, as illustrated in FIG. 2 and FIG. 5. FIG. 2 shows the preferred embodiment having an external envelope 46, an internal envelope 48, and three medium envelopes individually referred to as an external absorption envelope 50, a vapor barrier envelope 52, and an internal absorption envelope 54. FIG. 3 shows a transverse sectional view taken on line 3—3 of FIG. 2, illustrating the concentric relation of the plurality of envelopes 46, 48, 50, 52, and 54.

A cross-sectional view of a portion of sleeve 24 is shown in FIG. 2. A pair of seam edges 55 of sleeve 24 is shown bound together by a plurality of overlock stitches and a plurality of reinforcing straight stitches. External envelope 46 is an extension of sleeve 24, as illustrated in FIG. 2 and FIG. 5.

Figure 6:
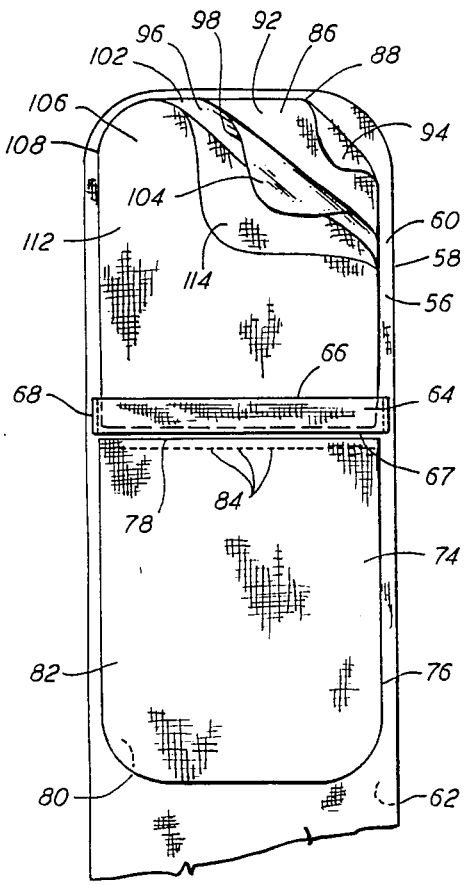

A further detailed description of the structure of sleeve 24 and control end 28, in accordance with the present invention, is best presented by describing the process for constructing the same. Referring to FIG. 6, a perspective view of partially constructed sleeve 24 and control end 28 is shown. An external sheet 56 comprises a boundary edge 58, interior surface 60, and an exterior surface 62. An elastic memeber 64, comprising a pair of side edges 66, 67 and a pair of opposing marginal edges 68, is placed upon and across external sheet 56 and fastened thereto adjacent to marginal edges 68 as illustrated in FIG. 6.

An internal sheet 74 comprises a boundary edge 76, a base edge 78, an interior surface 80, and an exterior surface 82, as illustrated in FIG. 6. Internal sheet 74 is disposed upon external sheet 56, such that interior surface 80 of internal sheet 74 faces interior surface 60 of external sheet 56, and base edge 78 is disposed parallel and adjacent to side edge 67 of elastic member 64, as illustrated in FIG. 6. Internal sheet 74 is seamed to external sheet 56 by a plurality of stitching 84 disposed in parallel arrangement with and adjacent to base edge 78 as illustrated in FIG. 6.

Figure 4:
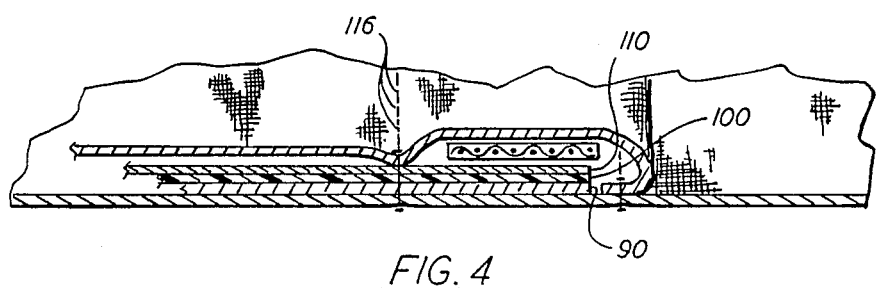
FIG. 4 is an enlarged sectional view showing a portion of the view depicted in FIG. 2, illustrating detailed construction of the control end of the present invention.

An external absorption sheet 86 comprises a boundary edge 88, a base edge 90, an interior surface 92, and an exterior surface 94 as illustrated in FIG. 4 and FIG. 6. A vapor barrier sheet 96 comprises a boundary edge 98, a base edge 100, an interior surface 102, and an exterior surface 104, as illustrated in FIG. 4 and FIG. 6. An internal absorption sheet 106 comprises a boundary edge 108, a base edge 110, an interior surface 112, and an exterior surface 114, as illustrated in FIG. 4 and FIG. 6.

The vapor barrier sheet 96 is superposed upon external absorption sheet 86, such that exterior surface 104 of vapor barrier sheet 96 faces interior surface 92 of external absorption sheet 86. Internal absorption sheet 106 is superposed upon vapor barrier sheet 96, such that exterior surface 114 of internal absorption sheet 106 faces interior surface 102 of vapor barrier sheet 96. The superposed sheets 86, 96, and 106 are collectively disposed upon external sheet 56, such that exterior surface 94 of external absorption sheet 86 faces interior surface 60 of external sheet 56, and set under elastic member 64, such that superposed base edges 90, 100, and 110 are parallel with and adjacent to side edge 67 and in opposing relation to base edge 78, as illustrated in FIG. 6.

As an alternative method, superposed sheets 86, 96 and 106 may be disposed upon external sheet 56 in the same orientation prior to fastening elastic member 64 to external sheet 56. Elastic member 64 may be disposed upon the superposed sheets 86, 96 and 106, such that side edge 67 of elastic member 64 is adjacent to and parallel with the superposed base edges 90, 100, and 110. Elastic member 64 may then be fastened to the superposed sheets 86, 96 and 106 and to external sheet 56, at opposing marginal edges 68 of elastic member 64.

After the superposed sheets, 86, 96 and 106 are collectively set under elastic member 64, as illustrated in FIG. 6, internal sheet 74 is pivoted about plurality of stitching 84 such that it substantially overlaps sheets 86, 96 and 106 and wraps elastic member 64. Internal sheet 74, internal absorption sheet 106, vapor barrier sheet 96, external absorption sheet 86, and external sheet 56 are commonly fastened together by a plurality of stitches 116 as illustrated in FIG. 7.

FIG. 8 is a fragmentary perspective view of sleeve 24 and control end 28 partially constructed according to the present invention, and shows no further construction than is shown in FIG. 7, except that sheets 74, 86, 96 and 106 are together pivotally displaced approximately one hundred eighty degrees to rest upon interior surface 60 of external sheet 56.

External sheet 56 may be represented in three sections. A front section 70 of external sheet 56 is defined by boundary edge 58 and by an imaginary straight line along plurality of stitches 116 projecting out to boundary edge 58, as illustrated in FIG. 8. A center section of external sheet 56 is defined by an imaginary straight line along plurality of stitches 116 projecting out to boundary edge 58, an imaginary straight line along plurality of stitches 84 projecting out to boundary edge 58, and boundary edge 58. A rear section 72 is defined as that remaining portion of external sheet 56, as best illustrated in FIG. 7.

The configuration as illustrated in FIG. 8 is rotated One Hundred Eighty Degrees (180°) about the longitudinal axis of external sheet 56 as depicted in FIG. 9. FIG. 9 shows the construction of external envelope 46. FIG. 9 shows exterior surface 62 of the rear section of external sheet 56 plain to view. The front section of external sheet 56 is folded such that a portion of exterior surface 62 is substantially enclosed, as illustrated in FIG. 9. A plurality of stitches 118 seam the folded front section of external sheets 56 together, adjacent to boundary edge 58, producing a pair of seam edges 120. Although not shown in FIG. 9, the pair of seam edges 120 may be bound together with a plurality of overlock stitches or a second plurality of straight stitches or both, as shown for example at 55 in FIG. 2.

The folded and seamed front section of external sheet 56, which is substantially in the form of a sheath, is pushed inside-out exposing exterior surface 62 as an outside surface as illustrated in FIG. 10. In this position, exterior surface 62 of the front section of external sheet 56 is made to face, generally, exterior surface 62 of the rear section of external sheet 56. The pair of seam edges 120 are now disposed in the interior of the folded and seamed front section of external sheet 56.

This completes the construction of external envelope 46 according to the present invention.

External absorption envelope 50 is constructed, according to the present invention by a similar process as described for external envelope 46. External absorption sheet 86 is pivoted about plurality of stitches 116 from its position depicted in FIG. 9. External absorption sheet 86 is folded such that external surface 94 is substantially enclosed, as similarly described for external envelope 46. A plurality of stitches 122 seam the folded external absorption sheet 86 together adjacent to boundary edge 88, producing a pair of seam edges 124. The pair of seam edges 124 may be bound together with a plurality of overlock stitches or a second plurality of straight stitches or both.

The folded and seamed external absorption sheet 86, which is substantially in the form of a sheath, is pushed inside-out and into the interior of external envelope 46, such that exterior surface 94 faces the interior surface of external envelope 46. The pair of seam edges 124 are now disposed in the interior of the folded and seamed external absorption sheet 86, as illustrated in FIG. 2. This completes the construction of external absorption envelope 50, according to the present invention.

Vapor barrier envelope 52 is constructed, according to the present invention, by a similar process as described for external envelope 46. Vapor barrier sheet 96 is pivoted about plurality of stitches 116 from its position depicted in FIG. 9. Vapor barrier sheet 96 is folded such that exterior surface 104 is substantially enclosed, as similarly described for external envelope 46. A plurality of stitches 126 seam the folded vapor barrier sheet 96 together adjacent to boundary edge 98, producing a pair of seam edges 128. The pair of seam edges 128 may be bound together with a plurality of overlock stitches or a second plurality of straight stitches or both.

The folded and seamed vapor barrier sheet 96, which is substantially in the form of a sheath, is pushed inside-out and into the interior of external absorption envelope 50, such that exterior surface 104 faces the interior surface of external absorption envelope 50. The pair of seam edges 128 are now disposed in the interior of folded and seamed vapor barrier sheet 96 as illustrated in FIG. 2. This completes the construction of vapor barrier envelope 52.

Internal absorption envelope 54 is constructed, according to the present invention, by a similar process as described for external envelope 46. Internal absorption sheet 106 is pivoted about plurality of stitches 116 from its position depicted in FIG. 9. Internal absorption sheet 106 is folded such that exterior surface 114 is substantially enclosed, as similarly described for external envelope 46. Plurality of stitches 130 seam the folded internal absorption sheet 106 together adjacent to boundary edge 108, producing a pair of seam edges 132. The pair of seam edges 132 may be bound together with a plurality of overlock stitches or a second plurality of straight stitches or both.

The folded and seamed internal absorption sheet 106, which is substantially in the form of a sheath, is pushed inside-out and into the interior of vapor barrier envelope 52, such that exterior surface 114 faces the interior surface of vapor barrier envelope 52. The pair of seam edges 132 are now disposed in the interior of folded and seamed internal absorption sheet 106 as illustrated in FIG. 2. This completes the construction of internal absorption envelope 54.

Internal envelope 48 is constructed according to the present invention as follows. Internal sheet 74 is pivoted about plurality of stitches 116 from its position depicted in FIG. 9. Internal sheet 74 is folded such that interior surface 80 is substantially enclosed, as illustrated in FIG. 11. Internal sheet 74 is therefore folded in a reverse manner relative to the manner of folding external sheet 56. A plurality of stitches 134 partially seam the folded internal sheet 74 together adjacent to boundary edge 76, causing an opening 136 to be defined by the remaining unseamed portion of boundary edge 76 and a rim 138 bounded by plurality of stitches 116, as illustrated in FIG. 11. The seamed portions of boundary edge 76 produce a pair of seam edges 140. The pair of seam edges 140 may be bound together with a plurality of overlock stitches or a second plurality of straight stitches or both.

The folded and seamed internal sheet 74 is pivoted further in a clockwise direction about plurality of stitches 116 from its position depicted in FIG. 11, and tucked inside internal absorption envelope 54, such that exterior surface 82 faces the interior surface of internal absorption envelope 54. The pair of seam edges 140 remain externally projecting from the folded and seamed internal sheet 74, such that they face the interior surface of internal absorption envelope 54, as illustrated in FIG. 2, FIG. 3 and FIG. 5. The resulting configuration is illustrated in FIG. 12. This completes the construction of internal envelope 48.

Concentrically disposed envelopes 46, 48, 50, 52, and 54 are collectively pulled inside-out, as one unit, as illustrated in FIG. 13. The interior surface of internal envelope 48 and interior surface 60 of external sheet 56 at rear section 72 are substantially fully exposed. Seam edges 140 of internal envelope 48 are now internally projecting. The remaining unseamed portion of boundary edge 76 is folded inwardly to correspond in orientation with internally projecting seam edges 140. The rear section 72 of external sheet 56 is folded together at boundary edge 58, and a plurality of stitches 142 are caused to seam the folded rear section 72 together, adjacent to boundary edge 58, producing a pair of seam edges 55, as illustrated in FIG. 2 and FIG. 13.

A wrap region 144 of internal sheet 74, is defined by base edge 78, constituting one side edge, a line along plurality of stitches 116, constituting an opposing side edge, and that portion of boundary edge 76 situated between the opposing side edges, constituting opposing end edges 146, as illustrated in FIG. 2.

Referring to FIG. 13, folded wrap region 144, folded elastic member 64, and the center section of external sheet 56, are fastened together by plurality of stitches 142, adjacent to opposing end edges 146, opposing marginal edges 68, and that portion of boundary edge 58 that completes the center section.

An alternative procedure includes fastening together only folded wraped region 144 and the center section of external sheet 56. This alternative procedure is realized by dimensioning internal sheet 74 such that base edge 78 extends beyond opposing marginal edges 68 once fastened to external sheet 56, as shown in FIG 6. Accordingly, opposing end edges 146 of wrap region 144 extend beyond opposing marginal edges 68. Thus, the center section of external sheet 56 and folded wrap region 144 may be fastened together by plurality of stitches 142.

As shown in FIG. 13, plurality of stitches 142 fasten together the inwardly folded remaining unseamed portion of boundary edge 76. The plurality of stitches 142 may be reinforced with a plurality of overlock stitches or a second plurality of straight stitches or both as generally illustrated in FIG. 13. The completed combination of sleeve 24 and control end 28 is attached to body clothing portion 22 by any conventional fastening method.

FIG. 14 illustrates an alternative embodiment of inventive garment 20, and is designated generally as 220. This embodiment is substantially similar to inventive garment 20 except that it further comprises a waist portion 223 having an elastic waist band 225, and a legs portion 227. Waist portion 223, waist band 225, and legs portion 227 are constructed in any conventional manner.

Body clothing portion 22, sleeves 24 and 26, external envelope 46 and internal envelope 48 of control ends 28 and 30 may be constructed of any material, including fabric material such as cotton twill, polyester and cotton blend open weave, and nylon. External absorption envelope 50 and internal absorption envelope 54 of control ends 28 and 30 may be constructed of any material, including fabric material such a terry cloth. Vapor barrier envelope 52 may be constructed of any material, including Roclon material, referred to by its product name, Black-Out. The preferred embodiments of the present invention are constructed such that they are completely washable by any conventional means.

The operation of the invention, as claimed, is as follows. Inventive garment 20 or inventive garment 220 is worn such that the placket opens up to the rear side of the wearer. The placket may be fastened together by Velcro fastening strips. Once the arms of the wearer are received through sleeves 24 and 26, a portion of the arm, the wrist and hand are substantially enclosed at control ends 28 and 30, as illustrated in FIG. 5. Plurality of envelopes 46, 48, 50, 52 and 54 are positioned, configured and dimensioned such that they are free and independent of one another. This property causes hand-activity to be hindered in that when the hand is flexed in an effort to grasp or manipulate an external object external envelope 46 will be substantially unresponsive to internal envelope 48 being driven by the flexed hand, as illustrated in FIG. 5. In addition to this principle, the general sheath-shaped envelopes contribute to the objective of controlling and hindering hand-activity.

External absorption envelope 50 adjoins external envelope 46 such that any moisture penetrating external envelope 46 is substantially absorbed by external absorption envelope 50. This absorption mechanism facilitates the drying of the outside surface of external envelope 46, thus discouraging the compulsive action of moistening the outside surface of the enclosure to aid in collecting foreign substances such as soil, hair, and paper.

Internal absorption envelope 54 adjoins internal envelope 48 such that any moisture penetrating internal envelope 48 is substantially absorbed by internal absorption envelope. This absorption mechanism facilitates absorption of perspiration from the hand of the wearer.

Vapor barrier 52 is disposed between external absorption envelope 50 and internal absorption envelope 54. Vapor barrier 52 acts to substantially repel any moisture reaching it from internal absorption envelope 54 and external absorption envelope 50. Vapor barrier 52 acts as a shield for the hand of the wearer from exposure to water or saliva.

The unraveling and shredding of the inventive garment is substantially precluded by the unique opposing arrangement of the pair of seam edges 120 of external envelope 46 and the pair of seam edges 140 of internal envelope 48. As can be seem from FIG. 2 and FIG. 5, seam edges 120 are in opposing relation to seam edges 140. Seam edges 140 are disposed on the outside surface of internal envelope 48 and away from the hand and fingers. Seam edges 120 are disposed on the interior surface of external envelope 46 and shielded from external forces. Accordingly, the stitching used to construct control ends 28 and 30 are shielded from the wearer's fingers, teeth, etc. In addition, the wearer of inventive garment 20 or 220 is further discouraged from unraveling and shredding said garments by use of overlock stitching or additional reinforcing straight stitching or both.

The use of a raglan type sleeve also hampers the wearer in his or her efforts to shed the inventive garment. Also, the positioning of the placket on the rear side of the garment further discourages the wearer from shedding the garment.

Typical embodiments of the present invention have been described herein and shown in the accompanying drawings to illustrate the underlying principles of the invention, but it is to be understood that numerous modifications may be made to the structure and methods herein disclosed without departing from the broad spirit and scope of the invention.

I claim:

1. A method of making a sleeve member comprising the steps of:
   (a) disposing a plurality of superposed sheets of fabric material upon a front section of an external sheet, each sheet of said plurality of sheets and said external sheet having an exterior surface and an interior surface, said plurality of sheets being orientated such that their exterior surfaces face the interior surface of said external sheet;

(b) fastening one edge of an internal sheet to a rear section of said external sheet in opposing relation to said plurality of sheets, said internal sheet having an exterior surface and an interior surface and being in a first position such that its interior surface faces said interior surface of said external sheet;

(c) pivoting said internal sheet about its fastened edge from said first position to a second position, whereby said internal sheet is substantially superposed upon said plurality of sheets and its exterior surface is facing said interior surface of said external sheet;

(d) fastening a first base portion of said internal sheet and a base portion of each of the sheets of said plurality of sheets to said front section of said external sheet;

(e) folding said front section of said external sheet such that its exterior surface is substantially enclosed;

(f) seaming the folded edges of said front section such as to produce an external envelope having an interior surface exposed;

(g) pushing said external envelope inside-out such that an exterior surface is exposed;

(h) folding, seaming and pushing inside-out each sheet of said plurality of sheets in the same manner as said front section, such as to produce a plurality of envelopes, one inside the other, and all of said plurality of envelopes inside said external envelope, each of said envelopes being in concentric relation to the other;

(i) folding said internal sheet such that its interior surface is substantially enclosed;

(j) seaming the folded edges of said internal sheet such as to produce an internal envelope having an exterior surface exposed;

(k) pivoting said internal envelope about said first base portion such as to align said internal envelope with said concentrically disposed envelopes; and (l) tucking said internal envelope inside the innermost envelope of said concentrically disposed envelopes.

2. A method of making a sleeve member comprising the steps of:

(a) fastening opposing ends of a strip member to an external sheet, adjacent to a front section of said external sheet;

(b) tucking a base portion of each of a plurality of superposed sheets of fabric material between said strip member and said external sheet, each sheet of said plurality of sheets and said external sheet having an exterior surface and an interior surface, said plurality of sheets being orientated such that their exterior surfaces face the interior surface of said external sheets;

(c) fastening one edge of an internal sheet to a rear section of said external sheet in opposing relation to said plurality of sheets, said internal sheet having an exterior surface and an interior surface and being in a first position such that its interior surface faces said interior surface of said external sheet;

(d) pivoting said internal sheet about its fastened edge from said first position to a second position, whereby said internal sheet is substantially superposed upon said plurality of sheets and its exterior surface is facing said interior surface of said external sheet;

(e) fastening a first base portion of said internal sheet and said base portion of each of the sheets of said plurality of sheets to said front section of said external sheet;

(f) folding said front section of said external sheet such that its exterior surface is substantially enclosed;

(g) seaming the folded edges of said front section such as to produce an external envelope having an interior surface exposed;

(h) pushing said external envelope inside-out such that an exterior surface is exposed;

(i) folding, seaming and pushing inside-out each sheet of said plurality of sheets in the same manner as said front section, such as to produce a plurality of envelopes, one inside the other, and all of said plurality of envelopes inside said external envelope, each of said envelopes being in concentric relation to the other;

(j) folding said internal sheet such that its interior surface is substantially enclosed;

(k) seaming the folded edges of said internal sheet such as to produce an internal envelope having an exterior surface exposed;

(l) pivoting said internal envelope about said first base portion such as to align said internal envelope with said concentrically disposed envelopes; and (m) tucking said internal envelope inside the innermost envelope of said concentrically disposed envelopes.

* * * * *